(12) United States Patent
Ravid (10) Patent No.: US 9,880,233 B2
(45) Date of Patent: Jan. 30, 2018

(54) METHODS AND APPARATUS TO DETERMINE PARAMETERS IN METAL-CONTAINING FILMS

(75) Inventor: Abraham Ravid, San Jose, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 846 days.

(21) Appl. No.: 13/095,279

(22) Filed: Apr. 27, 2011

(65) Prior Publication Data

US 2012/0274318 A1    Nov. 1, 2012

(51) Int. Cl.
| | | |
|---|---|---|
| *G01R 33/00* | (2006.01) | |
| *G01B 7/06* | (2006.01) | |
| *G01N 27/72* | (2006.01) | |
| *G01N 27/90* | (2006.01) | |

(52) U.S. Cl.
CPC ........... *G01R 33/007* (2013.01); *G01B 7/105* (2013.01); *G01N 27/72* (2013.01); *G01N 27/9033* (2013.01)

(58) Field of Classification Search
CPC ........................... G01N 27/72; G01N 27/9033
USPC ........................................................ 324/239
See application file for complete search history.

(56) References Cited

U.S. PATENT DOCUMENTS

| | | | | |
|---|---|---|---|---|
| 4,767,591 A | * | 8/1988 | Wampler | G01N 27/12 324/71.4 |
| 4,901,016 A | * | 2/1990 | Kusatani | G01R 33/14 324/210 |
| 4,950,990 A | * | 8/1990 | Moulder | B82Y 15/00 324/202 |
| 5,172,055 A | | 12/1992 | Horn | |
| 5,367,285 A | * | 11/1994 | Swinehart | H01C 1/14 204/192.21 |
| 5,559,428 A | * | 9/1996 | Li | G01B 7/06 324/671 |

(Continued)

OTHER PUBLICATIONS

Wang et al., "Calibration Methods of a 2 GHz Evanescent Microwave Magnetic Probe for Noncontact and Nondestructive Metal Characterization for Corrosion, Defects, Conductivity, and Thickness Nonuniformities", Review of Scientific Instruments, 76 054701 (2005).

(Continued)

*Primary Examiner* — Patrick Assouad
*Assistant Examiner* — Christopher McAndrew
(74) *Attorney, Agent, or Firm* — Moser Taboada; Alan Taboada (57) ABSTRACT

A method and apparatus to determine a parameter of a metal-containing film are provided herein. In some embodiments, a method of determining a parameter of a metal-containing film may include generating a first magnetic field by flowing an alternating current through a coil disposed adjacent to and spaced apart from the metal-containing film, wherein the first magnetic field induces a second magnetic field proximate the metal-containing film; heating the metal-containing film from a first temperature to a second temperature; measuring a response of the first magnetic field to the second magnetic field as the metal-containing film is heated from the first temperature to the second temperature; and correlating the response with a rate of temperature change of the metal-containing film as the metal-containing film is heated from the first temperature to the second temperature to determine a parameter of the metal-containing film.

19 Claims, 4 Drawing Sheets

(56) References Cited

U.S. PATENT DOCUMENTS

| | | | |
|---|---|---|---|
| 6,064,201 A | 5/2000 | Cha et al. | |
| 6,975,108 B2 | 12/2005 | Bilik et al. | |
| 7,112,960 B2 | 9/2006 | Miller et al. | |
| 7,204,639 B1* | 4/2007 | Gotkis | G01B 21/085 374/121 |
| 7,301,149 B2* | 11/2007 | MacKin | C23C 14/547 250/341.1 |
| 7,403,001 B1* | 7/2008 | Bailey, III | G01B 7/105 324/222 |
| 7,616,734 B1 | 11/2009 | Corbett et al. | |
| 7,795,865 B2* | 9/2010 | Fujita | B24B 37/013 324/229 |
| 7,795,866 B2* | 9/2010 | Fujita | B24B 37/013 324/229 |
| 7,821,257 B2* | 10/2010 | Fujita | B24B 37/013 324/229 |
| 7,830,141 B2* | 11/2010 | Fujita | G01B 7/105 324/229 |
| 2005/0122099 A1* | 6/2005 | Imamoto | G01N 27/82 324/239 |
| 2007/0072005 A1* | 3/2007 | Choi | B82Y 25/00 428/692.1 |
| 2007/0160107 A1* | 7/2007 | Gotkis | G01B 21/085 374/7 |
| 2009/0256558 A1* | 10/2009 | Fujita | G01B 7/105 324/230 |

OTHER PUBLICATIONS

Usanov et al., "Microwave Measurements of Thickness of Nanometer Metal Layers and Conductivity of Semiconductor in Structures "Metal-Semiconductor"",International Conference on Microwaves, Radar & Wireless Communication, May 22-24, 2006 pp. 1004-1107.

International Search Report and Written Opinion dated Nov. 1, 2012 for PCT Application No. PCT/US2012/034784.

* cited by examiner

METHODS AND APPARATUS TO DETERMINE PARAMETERS IN METAL-CONTAINING FILMS

FIELD

Embodiments of the present invention generally relate to methods and apparatus for determining parameters in metal-containing films.

BACKGROUND

Techniques to determine the thickness of metal-containing films can include using eddy current mapping. For example, a coil having an alternating current running through the coil can be brought into proximity with a metal-containing film. In response to a first magnetic field caused by the alternating current flowing through the coil, an opposing second magnetic field will be generated in the metal-containing film. The second magnetic field may be caused by an induced current, e.g., an eddy current, flowing along the metal-containing film. In embodiments where the metal-containing film may be about 1000 angstroms in thickness or greater, the aforementioned eddy current mapping technique can accurately measure the thickness of the metal-containing film. However, applying this technique to measure metal-containing films having thicknesses below about 500 angstroms, for example such as on the scale of hundreds or tens of angstroms requires high frequencies, such as in the gigahertz (GHz) range to completely eliminate measurement errors related to contributions from underlayer properties, such as current loops and doping.

Accordingly, methods and apparatus for determining parameters in metal-containing films, such as film thickness, are provided herein.

SUMMARY

Methods and apparatus to determine a parameter of a metal-containing film are provided herein. In some embodiments, a method of determining a parameter of a metal-containing film may include generating a first magnetic field by flowing an alternating current through a coil disposed adjacent to and spaced apart from the metal-containing film, wherein the first magnetic field induces a second magnetic field proximate the metal-containing film; heating the metal-containing film from a first temperature to a second temperature; measuring a response of the first magnetic field to the second magnetic field as the metal-containing film is heated from the first temperature to the second temperature; and correlating the response with a rate of temperature change of the metal-containing film as the metal-containing film is heated from the first temperature to the second temperature to determine a parameter of the metal-containing film.

In some embodiments, an apparatus includes a system for determining a parameter of a metal-containing film disposed on a substrate may include a substrate support comprising the metal-containing film; one or more coils positionable at least one of above or below the substrate support; an alternating current power source coupled to the one or more coils to provide an alternating current through the one or more coils to generate a first magnetic field proximate the metal-containing film when the substrate is disposed on the substrate support; an energy source to provide energy to the metal-containing film, when the substrate is present on the substrate support, sufficient to heat the metal-containing film; and a controller to determine a parameter of the metal-containing film based on a response of the first magnetic field to a second magnetic field induced by the first magnetic field over a temperature range of the metal-containing film.

Other and further embodiments of the present invention are described below.

BRIEF DESCRIPTION OF THE DRAWINGS

Embodiments of the present invention, briefly summarized above and discussed in greater detail below, can be understood by reference to the illustrative embodiments of the invention depicted in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Methods and apparatus to determine a parameter of a metal-containing film are disclosed herein. Embodiments of the inventive methods and apparatus may advantageously facilitate determination of one or more parameters in metal-containing films. For example, in some embodiments, the inventive methods and apparatus may be used to determine a film thickness and/or a thickness ratio of component layers in a metal-containing film having a thickness of less than about 1000 angstroms.

Figure 1:
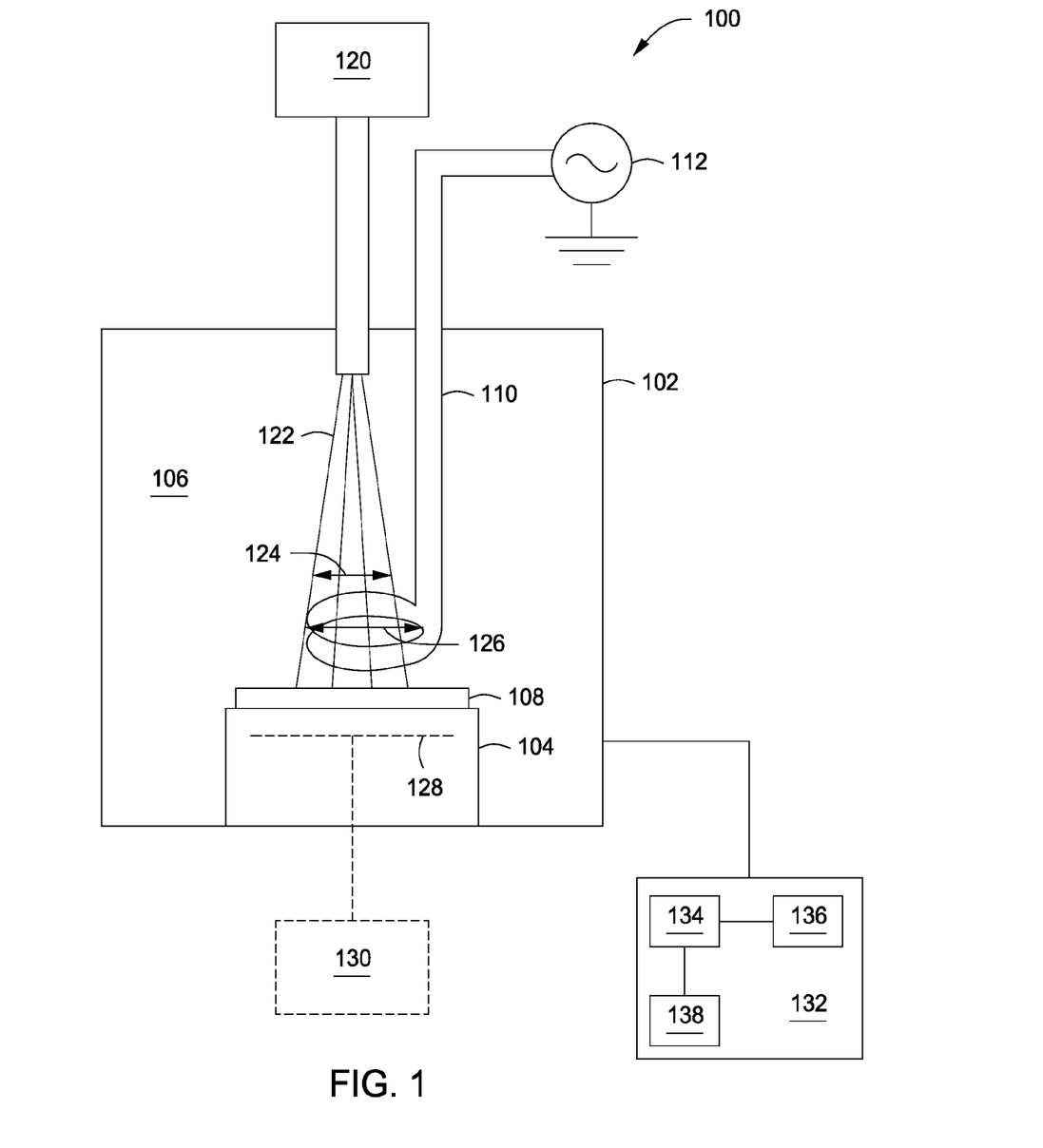
FIG. 1 depicts a system for determining a parameter in a metal-containing film in accordance with some embodiments of the present invention.

At least some embodiments of the inventive method may be performed in a chamber having a support for supporting a substrate having a metal-containing film to be measured disposed in the chamber, a coil for generating a magnetic field proximate the substrate, and a heat source for heating the metal-containing film. The chamber may be any suitable chamber such as a process chamber where substrate processes may be performed (such as film deposition), a metrology chamber, for example, to measure film properties before or after processing has been performed on the film, or the like. Alternatively, the apparatus may be part of a support to support a substrate, such as a substrate transfer robot or the like. The apparatus may be used as described herein to determine one or more parameters of the metal-containing film. FIG. 1 depicts one such exemplary system for determining one or more parameters of a metal-containing film in accordance with some embodiments of the present invention. The system 100 includes a chamber 102 having a substrate support 104 disposed within an inner volume 106 of the chamber 102. A substrate 108 may be disposed on the substrate support 104. The substrate 108 may be the metal-containing film, or the metal-containing film may be disposed on the substrate 108.

The system 100 further includes a coil 110 positionable at least one of above or below the substrate support 104. The coil 110 may be positionable above the substrate support 104 and substrate 108 as shown in FIG. 1. However, the chamber 102 and the substrate support 104 are merely exemplary embodiments of the present invention. For example, as illustrated in FIG. 2B and discussed below, embodiments of the present invention may include partial substrate supports, such as including a ring to support the substrate along a peripheral edge while exposing both an upper and lower surface of the substrate.

Returning to FIG. 1, the substrate support 104 may be positionable with respect to the coil 110, for example, having a lift mechanism or the like (not shown) for raising and lowering the substrate support 104. Further, in embodiments where the apparatus, includes a chamber, such as chamber 102, the substrate support 104 may include a rotation mechanism to rotate the substrate.

The coil 110 may be made of any suitable conductive material, and may have any suitable shape or number of rotations necessary to generate a magnetic field having a desired shape, frequency, and magnitude when power is applied to the coil 110. The coil 110 may be independently movable in both the perpendicular and parallel directions with respect to the surface of the substrate 108, for example, to adjust the proximity of the generated magnetic field relative to the surface of the substrate and/or to move the coil 110 to a portion of the substrate having the metal-containing film to be measured. Alternatively or in combination, the substrate support 104 may be moved relative to the coil 110.

The eddy current-based signal changes with the distance to the surface to be measured. Accordingly, in order to obtain an accurate thickness determination, the gap between the coil 110 and the substrate surface must be maintained at a fixed level, or alternatively, measured and used to introduce a correction factor to the reading. The measurement of the distance between the coil 110 and the substrate surface may be measured using a proximity sensor (not shown). The proximity sensor may operate in any suitable manner, including but not limited to using interference of light, either a laser or a broadband illumination, a capacitance sensor, a dedicated eddy current sensor for this purpose, or the like.

An alternating current may be provided to the coil 110 by a power source 112 coupled to the coil 110. The power source 112 may supply any suitable range of frequencies, for example, such as those frequencies in the radio frequency (RF) range. In some embodiments, the power source 112 may provide alternating current at frequencies ranging from 60 kHz to about 5 MHz.

Figure 2A:
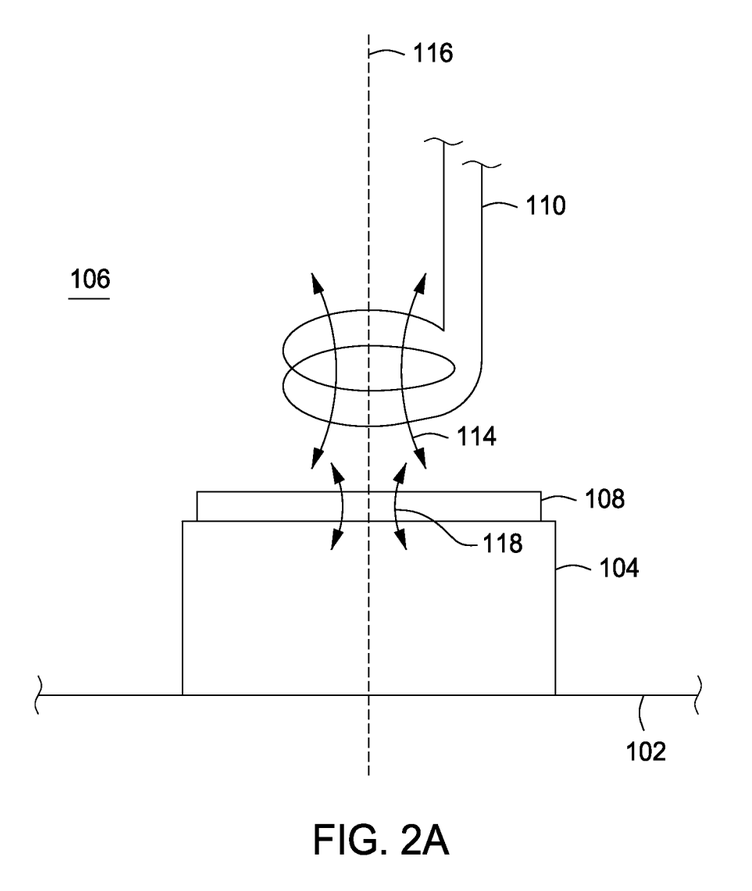
FIG. 2A depicts a partial view of the system in FIG. 1 in accordance with some embodiments of the present invention.
Figure 2B:
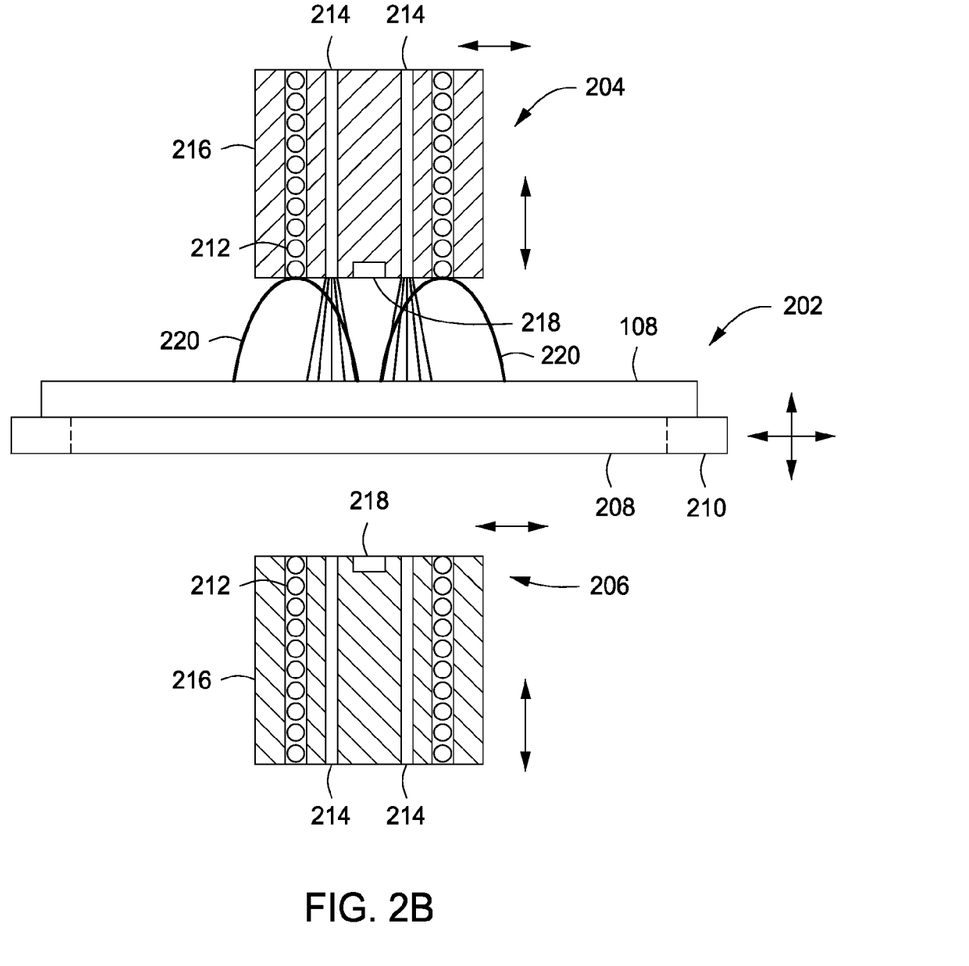
FIG. 2B depicts a partial view of a system for determining a parameter in a metal-containing film in accordance with some embodiments of the present invention.

In operation, and as illustrated in FIG. 2A, the alternating current power source 112 coupled to the coil 110 can provide the alternating current through the coil 110 to generate a first magnetic field 114 proximate an upper surface of the substrate 108 when the substrate 108 is disposed on the substrate support 104. The coil 110 may have a central axis 116 perpendicular to a surface of the substrate 108. The alternating current flowing through the coil 110 may generally flow about the central axis 116. The first magnetic field 114 may be oriented along the central axis 116, as shown in FIG. 2A. However, the shape and general orientation of the first magnetic field as illustrated in FIG. 2A is merely exemplary, and the first magnetic field 114 may have any suitable shape in accordance with the shape of the coil 110 necessary to provide a first magnetic field 114 that is capable of inducing a response in the substrate 108.

For example, an induced response may include an induced current, such as an eddy current or the like, in the substrate 108 (e.g., a metal-containing film). For example, the induced current in the substrate 108 may flow about the surface of the substrate 108 in an opposing direction to the alternating current of the coil 110. The induced current may give rise to a second magnetic field 118. Similar to the first magnetic field 114, the second magnetic field 118 may be oriented along the central axis 116 and opposing the first magnetic field 114. However, the shape and general orientation of the second magnetic field shown are merely exemplary as illustrated, and the actual shape and general orientation may vary dependent upon any one or more of several factors, such as the shape and general orientation of the first magnetic field 114 and/or the shape, crystal structure, and general orientation of the substrate 108.

The second magnetic field 118 may generally oppose the first magnetic field 114. In addition, the second magnetic field 118 may cause a change in the first magnetic field 114 which can result in a corresponding change in the alternating current flowing through the coil 110. For example, such a change in the alternating current flowing through the coil 110 may include a change in the impedance of the alternating current flowing through the coil 110 or the like. The change in the alternating current flow through the coil 110 may be determined by a sensor (not shown), feedback loop or any suitable known methods for monitoring and/or determining one or more aspects of the alternating current flowing through the coil 110. For example, methods for determining aspects of alternating current flowing through coils may be found in U.S. Pat. No. 4,000,458, titled "Method for the Noncontacting Measurement of the Electrical Conductivity of a Lamella" issued Dec. 28, 1976.

Returning to FIG. 1, the system 100 may include an energy source to provide energy to the substrate 108 when disposed on the substrate support 104 to heat the substrate 108. For example, the substrate 108 may be heated by the energy source and a response of the first magnetic field 114 to the induced second magnetic field 118 may be measured. The response of the first magnetic field 114 to the second magnetic field 118 may be a function of a temperature of the substrate 108, the amount of energy input to the substrate 108 by the energy source, combinations thereof, or the like. For example, a method 300 of heating the substrate 108 and measuring a response of the first magnetic field 114 is discussed below.

The energy source may be any suitable energy source that is capable of heating the substrate 108 in a controlled manner. For example, the energy source may be a light source disposed at least one of above or below a substrate support as illustrated in FIGS. 1 and 2B. For example, in some embodiments, the energy source may be a light source 120 disposed above the substrate support 104 as illustrated in FIG. 1. In some embodiments, the light source 120 may be focused into a beam 122 having a diameter 124 (e.g., a first diameter) that is substantially equivalent to a diameter 126 (e.g., a second diameter) of the coil 110. For example, the first and second diameters 124, 126 may be substantially equivalent to locally deliver a known amount of energy to a portion of the substrate 108 over which the coil 110 is disposed. The light source 120 may be any suitable light source as discussed above, for example, such as a laser, a quartz halogen lamp, a fiber optic bundle, a minilamp, or the like.

Alternatively or in combination, the energy source may be a heating element disposed at least one of above or below a substrate support as illustrated in FIGS. 1 and 2B. For example, the heating element may be a resistive or inductive heating element, such as a heating element 128 disposed in the substrate support 104. Alternatively, the heating element may be disposed above or below the substrate, for example, the coil 110 may be further used to inductively heat the substrate 108 or a separate element (not shown) disposed adjacent to the coil 110 may be used to heat the substrate 108.

The heating element 128 may be any suitable size and shape necessary to provide an amount of energy to a portion of the substrate 108 disposed below the coil 110. For example, in some embodiments, the heating element 128 may be suitably sized to heat the entire substrate 108. Alternatively, in some embodiments, the heating element 128 may be configured to heat a portion of the substrate 108 having a diameter substantially equivalent to the second diameter 126 of the coil 110. For example, the heating element 128 may further comprise a plurality of heating elements wherein each heating element in the plurality is configured to heat a portion of the substrate 108 having a diameter substantially equivalent to the second diameter 126 of the coil 110. For example, the coil 110 may be placed above a given portion of the substrate 108 having one of the plurality of heating elements disposed below the given portion to determine the parameter of the metal-containing film at the given portion as a function of temperature, energy input, or the like, as described herein. The heating element 128 may alternatively, or in combination with embodiments illustrated in FIG. 1, be disposed in the coil 110, be the coil 110 itself, or be a separate element disposed adjacent to the coil 110.

The heating element 128 may be coupled to a power source 130 to provide a current to the heating element 128. For example, the power source 130 may provide any suitable current necessary to generate heat from the heating element 128. In operation, a controller, for example a controller 132 as discussed below, may control the alternating current power source 112 and the power source 130 to provide power to only one of the coil 110 or the heating element 128 at a given time. For example, alternating the current provided by the sources 112, 130 may facilitate reducing or eliminating any effect that a current provided to the heating element 128 may have on the current flowing through the coil 110.

The system 100 may include the controller 132 which generally comprises a central processing unit (CPU) 134, a memory 136, and support circuits 138. The controller 132 may be coupled to and may control the chamber 102 and various system components, such as the coil 110, the power source 112, and the like, directly (as shown in FIG. 1) or, alternatively, via computers (or controllers) associated with the chamber and/or the support systems. The controller 132 may be one of any form of general-purpose computer processor that can be used in an industrial setting for controlling various chambers and sub-processors. The memory, or computer-readable medium, 136 of the CPU 134 may be one or more of readily available memory such as random access memory (RAM), read only memory (ROM), floppy disk, hard disk, or any other form of digital storage, local or remote. The support circuits 138 are coupled to the CPU 134 for supporting the processor in a conventional manner. These circuits include cache, power supplies, clock circuits, input/output circuitry and subsystems, and the like. The memory 136 stores software (e.g., source or object code) that may be executed or invoked to control the operation of the system 100 in the manner described herein, for example, to perform the method 300 described below. For example, the controller 132 may control the system 100 to determine a parameter of the substrate 108 disposed on the substrate support 104 based on a response of the first magnetic field 114 to a second magnetic field 118 induced by the first magnetic field 114 over a temperature range of the substrate 108.

FIG. 2B depicts a partial view of a system 200 for determining a parameter in a metal-containing film in accordance with some embodiments of the present invention. The embodiments of the system 200 as illustrated in FIG. 2B may be applied interchangeably with the embodiments of the system 100 of FIG. 1. For example, embodiments of the substrate support 202 may be used in the chamber 102 or the like. Similarly, embodiments of a coil assembly 204, 206 may be used in chamber 102 in place of the light source 128 or heating element 128 and the coil 110. Further, as discussed above, the systems 100, 200 need not be confined to chambers, and may be disposed in designated metrology apparatus, such as metrology stations or chambers, or in other substrate handling devices, such as a substrate transfer robot or the like.

The system 200 includes the substrate support 202 and one or more coil assemblies 204, 206. As illustrated in FIG. 2B, two coil assemblies are shown disposed above and below the substrate support 202. However, this is merely one exemplary embodiment. In some embodiments, the system 200 may include one or more coil assemblies disposed at least one of above or below the substrate support 202. As shown in FIG. 2B, the coil assemblies 204, 206 may be positionable with respect to the substrate support 202. For example, the coil assemblies 204, 206 may by movable in directions parallel and perpendicular to the substrate support 202. Similarly, the substrate support 202 may be movable with respect to the coil assemblies 204, 206. For example, the substrate support 202 may be movable in directions parallel and/or perpendicular to the surface of the substrate 108 (e.g., horizontally and/or vertically).

The substrate support 202 may be movable with respect to the coil assemblies 204, 206 as shown in FIG. 2B. In some embodiments, the substrate support 202 may include a susceptor plate 208 which supports the lower surface of the substrate 108. For example, the susceptor plate 208 may be used with any of the embodiments disclosed herein, for example, when the coil assemblies are located above, below, or both above and below the substrate support 202. For example, the susceptor plate 208 may be made of any suitable material that does not interfere with inducing a magnetic field on the substrate 108 or making measurements based on the induced magnetic field. Alternatively, as illustrated by dotted lines in FIG. 2B, the substrate support 202 may include a ring 210 to support the substrate 108 about a peripheral edge of the substrate 108.

In some embodiments, the coil assemblies 204, 206 may each include a coil 212 and a light source 214. However, these embodiments are merely exemplary and other embodiments are possible. For example, in some embodiments, the coil 212 itself may serve the dual function of inducing a magnetic field proximate the substrate 108 as well as heating the substrate 108, for example, by resistive or inductive heating or the like. Alternatively, as discussed above (not shown in FIG. 2B) the light source 214 may be substituted by a heating element that may be disposed in the substrate support 202 to heat the substrate 108.

The light source 214 and the coil 212 may be disposed in a housing 216. For example, the housing may be cylindrical, or any suitable shape to accommodate the coil 212 and the light source 214. In some embodiments, the housing 216 may be a cylinder. In some embodiments, the housing may be made of a material suitable to facilitate shaping the magnetic field distribution, for example, comprising a suitable ferromagnetic material, such as MN8CX (a general purpose Mn—Zn ferrite material commercially available from Ceramic Magnetics, Inc.).

The light source 214 may be similar to embodiments of the light source 128 as discussed above. For example, the light source 214 may comprise a fiber optic bundle, or the like to provide light energy to raise the temperature of the substrate 108. The coil assemblies 204, 206 may include an infrared (IR) sensor 218. For example, the infrared sensor 218 may measure infrared radiation emitted from the substrate 108 as the substrate is heated to determine the temperature of the substrate 108. Similar to embodiments discussed above, the light source 214 may illuminate a surface that may be aligned with the coil 212. In some embodiments, the diameter of the illuminated area of the surface may be substantially equivalent to a diameter of the coil 212. In some embodiments, the shape and the range of the illuminated area may be selected to satisfy a requirement of a heat transfer calculation to increase the accuracy of the determination of the temperature of the layer. A magnetic field 220 provided by the coil 212 may be any suitable magnetic field as discussed above. For example, in some embodiments, the applied magnetic field 220 may have a bimodal cross section as shown in FIG. 2B.

Figure 3:
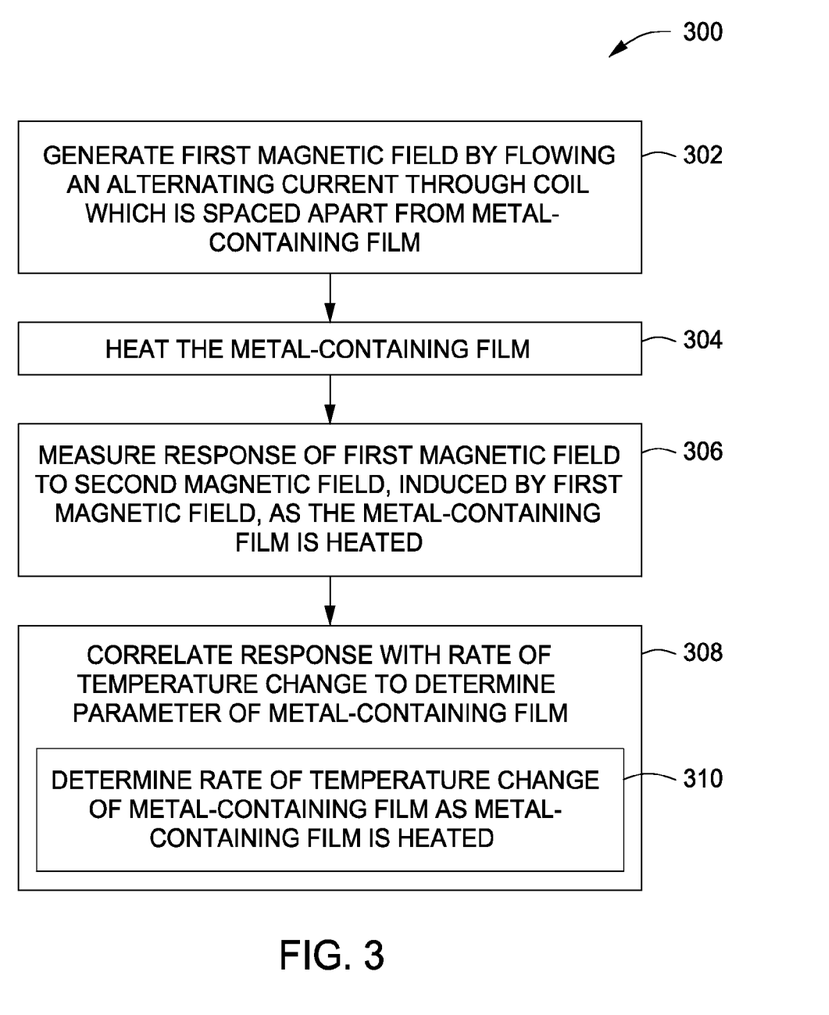
FIG. 3 depicts a flow chart of a method for determining a parameter in a metal-containing film in accordance with some embodiments of the present invention.

FIG. 3 depicts a flow chart of a method 300 for determining a parameter in a metal-containing film in accordance with some embodiments of the present invention. The method 300 is described below in accordance with embodiments of the system 100 depicted in FIGS. 1-2 and discussed above.

Figure 4:
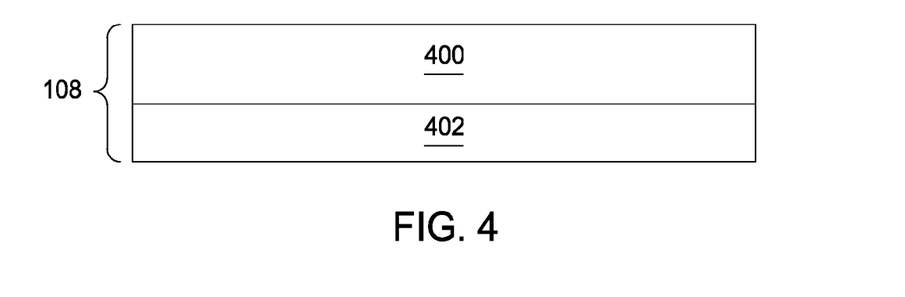
FIG. 4 depicts a metal-containing film in accordance with some embodiments of the present invention.

The method 300 begins at 302 by generating the first magnetic field 114 by flowing alternating current through the coil 110 which is disposed adjacent to and spaced apart from a metal-containing film (e.g., the substrate 108). For example, various embodiments of a metal-containing film are possible in accordance with the embodiments of the present invention. For example, the substrate 108 may illustratively include one or more of tantalum (Ta), copper (Cu), tantalum nitride (TiN), aluminum (Al), tungsten (W), titanium (Ti) or titanium nitride (TiN), although other metals may be used as well. For example, in some embodiments, the substrate 108 may include a metal-containing film including a metal layer 400, such as copper-containing layer or the like, disposed over a barrier layer 402, such as a tantalum-containing layer or the like as illustrated in FIG. 4. For example, the metal-containing film may be part of an interconnect structure, such as a trench or via formed in a dielectric layer to electrically couple, when filled with a conductive material, one portion of the substrate with another portion of the substrate. For example, the inventive methods may be utilized to determine an average thickness, sheet resistance, or other parameters of a metal-containing layer being deposited into a trench or via by electroplating or another suitable deposition technique.

As discussed above, the generation of the first magnetic field 114 induces the second magnetic field 118 proximate the metal-containing film (e.g., the substrate 108). The second magnetic field 118 may arise from an induced current, such as an eddy current or the like, in the metal-containing film that flows about a surface of the metal-containing film in an opposing direction to the alternating current of the coil 110. The induced current may change as a function of temperature in the metal-containing layer (e.g., the substrate 108). Changes in the induced current can be correlated to changes in temperature to determine parameters in the metal-containing film, such as thickness, composition, thickness ratio of component layers, or the like as discussed below. Further, the inventors have contemplated that geometric structure, crystalline properties, stress in the metal-containing film may be determined using the inventive methods disclosed herein.

At 304, the metal-containing film (e.g., the substrate 108) may be heated. In some embodiments, the substrate 108 may be heated by exposing the substrate 108 to an energy source, such as the laser beam 122 provided by the laser 120. Alternatively, or in combination, the resistive heating element 128 may also be used to heat the metal-containing film. The metal-containing film may be heated from a first temperature to a second temperature. The temperature range used may depend on the composition of the metal-containing film or the like. In some embodiments, the temperature may range from about room temperature to about 200 degrees Celsius. For example, for materials that may corrode, such as copper (Cu), the temperature range may be about room temperature to about 50 degrees Celsius. For example, for materials that may be corrosion resistant, such as tungsten (W), the temperature range may be up to about 200.

For example, the laser 120 may deliver a known amount of energy per unit time to an area of the substrate 108 having the metal-containing film, which may be used to locally control the temperature of the metal-containing film (e.g., to control the temperature of the metal-containing film in the area being heated). In some embodiments, the laser 120 may be desirable for heating the metal-containing film because the amount of energy per unit time it can deliver to an area of the substrate 108 can be well controlled. In some embodiments, the laser beam 122 may illuminate a surface aligned with the coil 110 and may have a diameter that is substantially equivalent to a diameter of the coil. For example, as illustrated in FIG. 1, the laser beam 122 may illuminate a surface of the substrate 108 that is approximately aligned with the coil 110, where the surface has a diameter that is substantially equivalent to the diameter of the coil 110. The diameters of the surface of the substrate 108 being heated and the diameter of the coil 110 may be substantially equivalent, for example, to ensure that a temperature rise due to laser beam 122 induced heating and the measurements made by the coil 110 can be well correlated as discussed below. For example, a measured response, such as impedance in the coil 110 due to the induced second magnetic field 118, may be correlated to a temperature, rate of temperature change, or the like, proximate the surface of the substrate 108 being illuminated by the laser beam 122 and not a temperature, rate of temperature change, or the like, averaged over the entire substrate 108.

Alternatively, as discussed above, the metal-containing film may be heated with a resistive heating element, such as the resistive heating element 128. For example, the metal-containing film can be heated by the resistive heating element 128 by flowing a current through the resistive heating element 128, for example from the power source 130. In some embodiments, the flow of the alternating current through the coil 110 is alternated with the flow of the current through the resistive heating element 128 such that the two currents are not provided concurrently.

At 306, a response of the first magnetic field 114 to the second magnetic field 118 may be measured as the metal-containing film is heated, for example, from the first temperature to the second temperature. For example, measuring a response may include measuring at least one of the impedance or resonance frequency of the alternating current through the coil 110 due to the presence of the opposing second magnetic field 118. From the at least one of the measured impedance or measured resonance frequency, for example, a resistivity of the metal-containing film may be determined. For example, known methods for determining aspects of alternating current flowing through coils may be found in U.S. Pat. No. 4,000,458, titled "Method for the Noncontacting Measurement of the Electrical Conductivity of a Lamella" issued Dec. 28, 1976.

Measuring a response of the first magnetic field may include measuring the response, such as impedance of the alternating current through the coil 110 or the like, a plurality of times over a time period as the metal-containing film is heated from the first temperature to the second temperature. For example, the response may be measured periodically as the metal-containing film is heated between the first and second temperatures, or at any suitable desired interval to obtain a measured response at several different temperatures of the metal-containing film.

At 308, the measured response may be correlated with a rate of temperature change to determine a parameter of the metal-containing film. For example, at 310, the rate of temperature change of the metal-containing film may be determined as the metal-containing film is heated from the first temperature to the second temperature. The rate of temperature change of the metal-containing film may differ from that of the measured response. For example, the rate of temperature change may be derived from contributions of one or more layers of the metal-containing film, such as the metal layer 400 and the barrier layer 402 discussed above or other layers disposed on the substrate, whereas the measured response may be derived from one or more conductive layers of the film, such as the metal-containing film or the metal layer 400. The rate of temperature change and the measured response may vary for other reasons as well. The rate of temperature change and the measured response may be correlated as discussed below to determine one or more parameters of the metal-containing film.

Similar to measurement methods discussed above for the measured response at 306, the rate of temperature change in the metal-containing film may be determined by measuring the temperature of the metal-containing film a plurality of times over the time period as the metal-containing film is heated form the first temperature to the second temperature. In some embodiments, a response of the first magnetic field 114 and the temperature of the metal-containing film may be measured simultaneously at a given time. For example, an array of data corresponding to the response versus temperature may be directly collected. Alternatively, the response and the temperature may be measured separately over the time period as the metal-containing film is heated and general trends in the behavior of the response and temperature can be determined over the time period. For example, a first set of data corresponding to a response versus time over the time period may be collected and a second set of data corresponding to a temperature versus time over the time period may be collected. The first and second sets of data may be correlated as discussed below.

In some embodiments, the time period for collecting data, such as the measured response and the temperature as discussed above at 306, 308, may begin when the metal-containing film is at the first temperature and end when the metal-containing film is at the second temperature. Alternatively, the time period for collecting data may be at any desired time period between the first and second temperatures for example, when the temperature of the metal-containing film has stabilized or reached a desired temperature between the first and second temperatures to begin measurements or based on readings from a sensor, such as the IR sensor 218.

Returning to 308, the measured response may be correlated with the rate of temperature change or sheet resistance change to determine a parameter of the metal-containing film. The parameter may include thickness of the metal-containing film, a ratio of thickness of the metal layer 400 to the barrier layer 402, or the like. The correlation at 308 may include modeling, for example, based on empirical data of component layers of the metal-containing film, such as resistivity as a function of temperature at known layer thicknesses for both the metal layer 400 and the barrier layer 402 or the like to match the trends measured for the metal-containing film at 306, 310 to within a desired tolerance level. For example, variable parameters in the model might include thicknesses of each of the metal layer 400 and the barrier layer 402 which may be optimized to fit the measured trends at 306, 310 to determine the thickness of each layer in the metal-containing film.

In some embodiments, the modeling process can involve one or more aspects. For example, one aspect may be to calculate the expected temperature change based on the overall thickness of the metal-containing film, for example, such as a copper layer (e.g., metal layer 400) disposed atop a barrier layer (e.g., barrier layer 402). Each layer can have a thermal conductivity, and the modeling process can consider the amount of energy absorbed in each layer, and the temperature increase rate associated with it. This modeling may be based on heat transfer calculations, and use available modeling tool such as finite element analysis.

In some embodiments, the modeling process may include some average structural property of the layer, such as trench depth and density, since trenches may act as fins, similar to an effective medium approximation.

In some embodiments, the modeling process may include, applying a pulse of light or inductive or resistive heating to the substrate and calculating the temperature rise, and fall. This can be done using the heat transfer calculations and/or finite element methods. Incorporating a detector (not shown in the Figures) to measure the temperature of the metal-containing layer based on the reflected heat, such as a bolometer or similar detector, may aid in calculation of the thickness of the metal-containing layer, for example, by using the measured temperature as an initial "guess" for the eddy current signal analysis. In some embodiments, the initial guess may be a first step in an iterative calculation to enhance accuracy, e.g., by modifying the pulse energy.

In some embodiments, a set of calibration wafers may be used, each having some change of known property (e.g., thickness or the like), to perfect the modeling process for a range of properties for which the modeling process is expected to work.

While the foregoing is directed to embodiments of the present invention, other and further embodiments of the invention may be devised without departing from the basic scope thereof.

The invention claimed is:

1. A method of determining a parameter of a metal-containing film, comprising:
generating a first magnetic field by flowing an alternating current through a coil disposed adjacent to and spaced apart from the metal-containing film, wherein the first magnetic field induces a second magnetic field proximate the metal-containing film;
heating the metal-containing film from a first temperature to a second temperature;
measuring the temperature of the metal-containing film at a plurality of times over a time period as the metal-containing film is heated from the first temperature to the second temperature;
determining a rate of temperature change based on the measured temperature;
measuring a response of the first magnetic field to the second magnetic field as the metal-containing film is heated from the first temperature to the second temperature; and
correlating the response with the rate of temperature change of the metal-containing film as the metal-containing film is heated from the first temperature to the second temperature to determine a thickness of the metal-containing film.

2. The method of claim 1, wherein the second magnetic field opposes the first magnetic field.

3. The method of claim 1, wherein an induced current in the metal-containing film flows about a surface of the metal-containing film in an opposing direction to the alternating current of the coil.

4. The method of claim 3, wherein the induced current changes as a function of the temperature of the metal-containing film.

5. The method of claim 1, wherein heating the metal-containing film further comprises:
delivering a known quantity of energy to the metal-containing film.

6. The method of claim 5, wherein heating the metal-containing film further comprises:
heating the metal-containing film with a light source.

7. The method of claim 6, wherein the light source illuminates a surface aligned with the coil and wherein a diameter of the surface illuminated by the light source is substantially equivalent to a diameter of the coil.

8. The method of claim 5, wherein heating the metal-containing film further comprises:
heating the metal-containing film with a heating element by flowing a current through the heating element, wherein the flow of the alternating current through the coil is alternated with the flow of the current through the heating element.

9. The method of claim 1, wherein measuring the response of the first magnetic field further comprises:
measuring at least one of impedance or resonance frequency of the alternating current through the coil.

10. The method of claim 9, further comprising:
determining a resistivity of the metal-containing film from at least one of the measured impedance or the measured resonance frequency.

11. The method of claim 1, wherein measuring the response of the first magnetic field further comprises:
measuring the response at a plurality of times over a time period as the metal-containing film is heated from the first temperature to the second temperature.

12. A method of determining a parameter of a metal-containing film, comprising:
generating a first magnetic field by flowing an alternating current through a coil disposed adjacent to and spaced apart from the metal-containing film, wherein the first magnetic field induces a second magnetic field proximate the metal-containing film;
heating the metal-containing film from a first temperature to a second temperature;
modeling the temperature of the metal-containing film over a time period based on an amount of energy provided to heat the metal-containing film from the first temperature to the second temperature;
determining a rate of temperature change based on the modeled temperature;
measuring a response of the first magnetic field to the second magnetic field as the metal-containing film is heated from the first temperature to the second temperature; and
correlating the response with the rate of temperature change of the metal-containing film as the metal-containing film is heated from the first temperature to the second temperature to determine a thickness of the metal-containing film.

13. The method of claim 1, wherein the time period begins when the metal-containing film is at the first temperature and ends when the metal-containing film is at the second temperature.

14. The method of claim 1, wherein the metal-containing film further includes a metal layer disposed atop a barrier layer.

15. The method of claim 14, wherein the second magnetic field results from an induced response in both the metal layer and the barrier layer and wherein the rate of change in the temperature of the metal-containing film results from heating both the metal layer and the barrier layer.

16. The method of claim 15, wherein a ratio of a thickness of the metal layer to a thickness of the barrier layer is correlated with the response with the rate of temperature change of the metal-containing film as the metal-containing film is heated from the first temperature to the second temperature.

17. A system for determining a parameter of a metal-containing film disposed on a substrate, comprising:
a substrate support to support a substrate comprising the metal-containing film;
one or more coils positionable at least one of above or below the substrate support;
an alternating current power source coupled to the one or more coils to provide an alternating current through the one or more coils to generate a first magnetic field proximate the metal-containing film when the substrate is disposed on the substrate support;
an energy source to provide energy to the metal-containing film, when the substrate is present on the substrate support, sufficient to heat the metal-containing film;
a sensor to measure a temperature of the substrate at a plurality of times over a time period as the metal-containing film is heated from a first temperature to a second temperature; and
a controller configured to:
determine a rate of temperature change based on the measured temperature; and
determine a thickness of the metal-containing film based on a correlated response with the rate of temperature change of the metal-containing film as the metal-containing film is heated from the first temperature to the second temperature.

18. The system of claim 17, wherein the energy source comprises:
a light source disposed at least one of above or below the substrate support, wherein the light source is focused into a beam having a diameter that is substantially equivalent to a diameter of the coil.

19. The system of claim 17, wherein the energy source comprises:
a heating element disposed at least one of above or below the substrate support; and
a power source to provide a current to the heating element, wherein the controller controls the alternating current power source and the power source to provide power to only one of the coil or the heating element at a given time.

* * * * *